United States Patent

Baudequin

[11] Patent Number: 5,290,529
[45] Date of Patent: Mar. 1, 1994

[54] METHOD OF TREATING SILICA FUMES FOR WHITENING PURPOSES

[75] Inventor: Francois Baudequin, Eaubonne, France

[73] Assignee: Electricite De France (Service National), France

[21] Appl. No.: 809,440

[22] Filed: Dec. 17, 1991

[30] Foreign Application Priority Data

Dec. 17, 1990 [FR] France ............... 90 15765

[51] Int. Cl.$^5$ ........................................ C01B 33/12
[52] U.S. Cl. ............................... 423/337; 422/139; 423/335
[58] Field of Search ............... 423/337, 335; 422/139, 422/145, 146, 147

[56] References Cited

U.S. PATENT DOCUMENTS 4,554,147 11/1985 Stoll et al. ..................... 423/335

FOREIGN PATENT DOCUMENTS 52-013497 1/1977 Japan .

OTHER PUBLICATIONS

Perry's Chemical Engineers' Handbook (6th Ed.), McGraw-Hill, N.Y. 1984, pp. 20-58 to 20-69.

*Primary Examiner*—Olik Chaudhuri
*Assistant Examiner*—Ken Horton
*Attorney, Agent, or Firm*—Blakely, Sokoloff, Taylor & Zafman

[57] ABSTRACT

The black powder to be treated is injected into the bottom portion of a heated dense fluidized bed, said bed having effective depth enabling the carbon the particles of silica to be oxidized into carbon dioxide as the particles go through the dense fluidized bed while being entrained by the fluidization air. The whitened powder is then recovered by filtering the gases leaving said dense fluidized bed. The invention is particularly applicable to the cosmetics industry for producing make-up that uses silica powder.

13 Claims, 1 Drawing Sheet

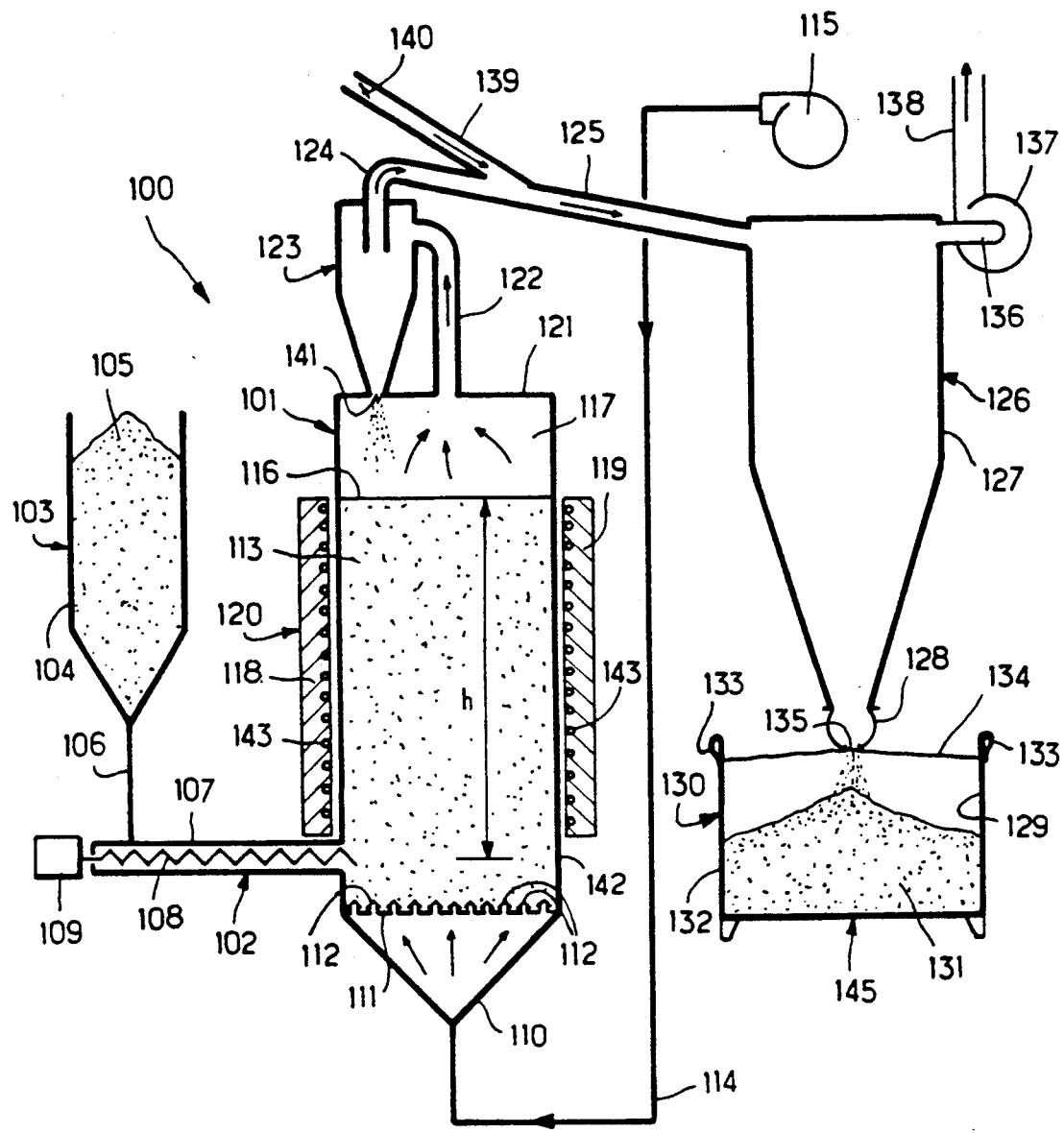

METHOD OF TREATING SILICA FUMES FOR WHITENING PURPOSES

The invention relates to processing silica fumes, and in particular the silica fumes that escape from electrical furnaces for producing silicon.

BACKGROUND OF THE INVENTION

The electrical furnaces used in the preparation of silicon are arc furnaces provided with graphite electrodes. Because of the very high temperatures and the flows of hot air inside such furnaces, a certain proportion of silicon escapes with the flue gases and oxidizes into silica fumes.

These fumes of silica, i.e. of $SiO_2$, have very small grain size (in the order of a few $\mu m$) and they are always black in color. This color is due essentially to the silica particles capturing carbon that comes from wear of the graphite electrodes.

The black color of these silica fumes makes them unsuitable for high value applications, in particular in the cosmetic industry, even though the existence of very fine grains urges people skilled in the art to seek an application that would make use of the advantages inherent in having silica powder supplied directly in the form of very fine grains.

There is therefore a need to whiten silica fumes so as to be able to make them more valuable.

However, the person skilled in the art encounters great difficulties with traditional incineration methods that are available, such as methods that make use of a rotating furnace or of a high-speed calcinator (also known as a "flash calcinator").

If a conventionally designed rotating furnace is used in the form of a rotating cylinder whose axis is at a small angle relative to the horizontal, with a flame being disposed at the inlet to or the outlet from the cylinder, it is observed that the substance injected into the cylinder to be turned over therein sticks together and reagglomerates into clusters of larger size, thus loosing its fineness.

This is explained by the fact that the two parameters of temperature and of contact time do not make it possible simultaneously to whiten the powder and to maintain the very fine grain size thereof. Since the contact time is de facto very short, either the temperature is selected to be quite low so as to avoid the particles sticking together, in which case the resulting powder is fairly gray in color, or else the temperature is raised in order to achieve satisfactory whitening, in which case the sintering temperature of the powder is exceeded and the resulting product is in the form of agglomerated lumps.

It would certainly be possible to provide an additional treatment system for reducing such agglomerated lumps to particles of a more acceptable grain size, but under such circumstances the method would be more expensive and in any event the geometry of the particles would be spoiled (crushed particles would be very rough and such lack of roundness would make them unsuitable for applications in which a very "smooth" powder is required, e.g. in the cosmetics industry as an ingredient in foundation make-up and face powder).

In addition, if a conventionally-designed flash calcinator is used which is in the form of a very tall narrow vertical cylinder with hot air being injected into the bottom thereof at high speed, although each grain of powder is individually supported to form an "entrained bed" and is subjected to a temperature that can be held below the sintering temperature (to avoid the particles sticking together), the powder remains in contact with high temperature air for too short a length of time (less than one second), such that the powder collected downstream from the calcinator is gray in this case also.

It would certainly be possible to increase the contact time by using a calcinator that is taller than the conventional height of existing calcinators (which is generally about 12 to 15 meters (m)), but that would lead to an enormous installation since it would have to be at least fifty meters tall.

Conventional methods thus do not make it possible to whiten silica fumes satisfactorily while retaining their very small grain size.

It should also be observed that the person skilled in the art would, a priori, avoid using any fluidized bed technique using hot gas with the powder to be treated since the grain size of the power is very much smaller than the limit of so-called "fluidizable" powders (generally 30 $\mu m$ to 50 $\mu m$). Under such circumstances the grains subjected to inter-particle forces and to the force of gravity can no longer be supported by a fluidization flow and it is not possible to prevent the powder blowing away.

An object of the invention is to solve this problem by providing a method of treatment and apparatus for implementing the method that enable silica fumes to be whitened while preserving the fine grain size, which has not been possible with conventional methods, as explained above.

Another object of the invention is to provide a method and apparatus for implementing the method suitable for use under financial conditions that are reasonable, without requiring a treatment installation of exorbitant size, and with the treatment process being suitable for automatic control.

Another object of the invention is to provide a method and apparatus for implementing the method making use of means having a structure that remains simple and reliable, thereby making it easy to connect the treatment installation to the rest of the factory, with the feed of silica fumes and the collection of the finished product being automated.

SUMMARY OF THE INVENTION

More particularly, the present invention provides a treatment method for treating silica fumes for whitening purposes, wherein the black powder to be treated is injected into the bottom portion of a heated dense fluidized bed, said bed having a predetermined effective depth between the injection level and the top surface of the bed that enables the carbon on the particles of silica to be oxidized into carbon dioxide as the particles pass through the dense fluidized bed while being entrained by the fluidization air, the whitened powder then being recovered by filtering the gases that come from said dense fluidized bed.

Preferably, the dense bed is a bed of sand whose effective depth is selected as a function of the mean diameter of the particles of silica to be treated.

It is then advantageous for the mean diameter of the particles of sand constituting the dense bed to be about 400 $\mu m$. In particular, the effective depth of the dense bed is about 1.5 meters when said bed is fluidized.

Preferably, the dense bed is heated via its outside surface by electrical heating. In an installation that is to treat a large tonnage of powder (e.g. more than three tons per hour), it is possible in a variant to provide electrical heating that is immersed within the fluidized bed, e.g. in the form of a conventional type of immersed heater element.

Advantageously, the dense bed is heated over its entire effective depth in such a manner that the fluidization air constitutes oxidizing air for oxidizing the carbon present in the silica fumes, the temperature of said bed nevertheless remaining below the sintering temperature of the powder to be treated.

Preferably, the temperature of the dense bed may be adjusted within the range about 550° C. to about 850° C. so as to oxidize all of the carbon without changing the crystal state of the silica fumes.

It is also advantageous for the gases coming from the dense fluidized bed to pass through a cyclone separator to return any particles of sand to the dense bed with filtering to recover the whitened powder being performed downstream from said cyclone separator.

It is then preferable for the separation performed by the cyclone separator to be obtained by selecting a cutoff diameter of about 30 $\mu$m for said cyclone separator.

It is also advantageous to provide for the gases leaving the cyclone separator to be subjected to dilution with cold air to reduce their temperature prior to said gases being filtered for recovering the whitened power. In particular, the temperature of the gases is reduced at least to 150° C. prior to filtering.

The invention also provides apparatus for implementing the above-specified treatment method, the apparatus being characterized by the fact that it comprises a closed vessel containing a dense fluidized bed which is fluidized by air feed means and which is maintained at a set temperature by associated heater means, means for injecting the black powder to be treated into the bottom portion of the dense fluidized bed, said bed having a predetermined effective depth between the injection level and the surface of said bed, and said vessel being extended upwards above the surface of the dense fluidized bed by a disengagement chamber which is connected to a separation circuit for recovering the whitened powder, said separation circuit including filter means for filtering the gases leaving said dense fluidized bed, and recovery means for recovering the whitened powder.

Preferably, the closed vessel is made of metal, and its outside wall is heated by electrical heater jacket members. In particular, the electrical heater jacket members extend over a height that is at least substantially equal to the predetermined effective depth of said dense fluidized bed. Thus, as mentioned above, it is possible in a variant to use a heater element immersed in the dense fluidized bed in large-scale installations.

It is also preferable for the closed vessel to contain a dense bed of sand whose effective depth is about 1.5 meters when said bed is fluidized, and to have a disengagement chamber whose height is several meters, and in particular not less than 3 meters. The diameter of the closed vessel is less critical, but it must nevertheless be greater than a minimum value to avoid any risk of forming a succession of solid-gas pistons which would hinder good heat exchange: for example, it would be possible under such circumstances to select a diameter of about one meter.

It is also advantageous for the air feed means to comprise a single feed duct connected to the closed vessel via the bottom thereof.

Also preferably, the means for injecting the black powder to be treated comprise a hopper and a substantially horizontal conveyor screw opening out into the inside of the closed vessel. However, in a large scale installation (e.g. for treating more than three tons per hour), it is preferable to provide a plurality of insertion points distributed around the periphery of the closed vessel so that the particles are uniformly distributed in the section of the dense fluidized bed.

It is also advantageous for the separation circuit to comprise a cyclone separator whose inlet is directly connected to the disengagement chamber of the closed vessel, with the cutoff diameter of said cyclone separator preferably being selected to be close to 30 $\mu$m.

Also preferably, the filter means are essentially constituted by a bag filter whose bottom portion terminates in a rotary lock having a container disposed thereneath constituting the recovery means, and whose upper portion is connected to an exhaust fan for evacuating the gases to a chimney. In particular, the bag filter is made of cloth, and has a cutoff diameter of not more than 1 $\mu$m.

Also advantageously, the duct connecting the outlet of the cyclone separator to the inlet of the bag filter includes an open branch connection enabling cold dilution air to be admitted into said duct. In which case, it is preferable for the branch connection to include a control member such as a flap for controlling the quantity of dilution air that penetrates into said duct.

BRIEF DESCRIPTION OF THE DRAWING

Other characteristics and advantages of the present invention appear more clearly in the light of the following description and the accompanying drawing, relating to a particular embodiment, the sole FIGURE of the drawing being a diagram of a treatment installation in accordance with the invention.

DETAILED DESCRIPTION

The treatment installation 100 shown in the single FIGURE comprises a closed vessel 101 containing a dense bed 113 fluidized by associated air feed means 111, 112, 114, and 115, and maintained at a set temperature by associated heater means 120.

The vessel 101 comprises an outside wall 142 which is cylindrical in this case, and is terminated by a substantially conical bottom 110, with the top of said vessel being closed by a top wall 121. The bed 113 is supported by a support grid 111 whose orifices are preferably fitted with "hatted" nozzles 112 of conventional design. These nozzles are welded to the grid and prevent the bed being siphoned downwards when the process is stopped (on stopping, small piles may thus form in the vicinity of the nozzles without a portion of the bed being siphoned downwards via the orifices as would happen with a simple flat grid, and this would be particularly disadvantageous on starting the process up again because of the risks of the grid being partially obstructed, thereby spoiling the velocity field of the fluidizing air). The fluidizing air is generated by a fan 111 connected to the bottom 110 of the vessel 101 by an associated duct 114.

The dense bed 113 is preferably a bed of sand having an effective depth h that is selected as a function of the mean diameter of the silica particles to be treated. The effective depth h corresponds to the height of the dense bed 113 between the top surface 116 of the bed and the level at which the powder to be treated is injected, i.e. in this case, the level at which an endless screw 108 opens out into the bed. A disengagement chamber 117 or bed ceiling is thus delimited between the top surface 116 of the bed and the top wall 121 of the closed vessel 101. For example, the dense bed 113 could be chosen to be constituted by particles of sand having a mean grain size of about 400 μm. Under such circumstances, the effective depth h of the dense bed 113 will be about 1.5 meters when the bed is fluidized (corresponding to a depth of about 1.3 meters when the installation is at rest, and the dense bed is not fluidized). Under such circumstances, the normal temperature and pressure (NTP) flow rate of fluidization air delivered by the fan 115 may be selected to be about 140 m³/h for a chamber having a diameter of about one meter.

The dense bed 113 may be heated from the outside as shown by electrical heater means which are preferably constituted in the form of heating jacket members 118 and 119 placed against the outside wall 142 of the closed vessel 101. Each of the heating jacket members than comprises a heater resistance 143, and two, or three, or even four shells may be used to make up a complete heating jacket that surrounds the outside wall of the closed vessel (in a variant, the jacket members could be rings threaded successively over the closed vessel). For a large-scale installation, i.e. an installation intended to treat more than three tons of powder per hour, the heating jacket members shown could be replaced by a heater element immersed within the dense bed, preferably coaxially therewith, so that the bed is then heated from the inside, and substantially from the axis of the closed vessel. The heating means 120 (constituted in this case by the heating jacket members 118 and 119) preferably extend over a height that is at least substantially equal to the predetermined effective depth h of the dense fluidized bed 113. The dense bed 113 is thus heated over its entire effective depth h so that all of the fluidization air is oxidizing air for oxidizing the carbon present in the silica fumes to be treated, the temperature of said bed nevertheless being chosen to be lower than the sintering temperature of the powder to be treated. The temperature of the dense bed must be chosen to be as high as possible so that a minimum contact time suffices to whiten the powder to be treated, thereby keeping the size of the closed vessel to as small a size as possible. In any event, the temperature must be less than the sintering temperature of the powder so as to avoid a phenomenon whereby the particles stick together into aggregates which would also have the effect of disrupting the hydrodynamics of the system. The regulated temperature of the dense bed 113 is preferably selected to lie in the range about 550° C. to about 850° C. so as to oxidize the carbon fully without changing the crystal state of the silica fumes. It should be observed that the dense fluidized bed 113 constitutes a so-called "infinitely mixed" bed, i.e. there is practically no temperature difference between different points within the dense bed. As a result, when the powder to be treated passes through the dense bed 113 by travelling up the effective depth h thereof, it is certain that the powder is treated uniformly, thereby ensuring that the desired white color is obtained for the particles that escape from said dense bed. The bed is thus a "bubble bed" insofar as the particles of sand remain geometrically confined in a well-defined volume without escaping therefrom. For example, the system can be controlled in such a manner that the temperature differences between the bottom of the bed in the vicinity of the supporting grid and a middle zone of the said bed do not exceed 20° C. It is thus possible to assume that the entire dense bed 113 is at a temperature that is uniform overall, and this is naturally favorable with respect to heat exchange. Finally, it may be observed that the closed vessel 101 constitutes a genuine isothermal reactor in this case.

When the closed vessel 101 contains a dense bed 113 of sand having an effective depth h of about 1.5 meters (depth of the fluidized bed), the disengagement chamber 117 may be given a height of a few meters, e.g. at least three meters. The diameter of the closed vessel 101 is less critical, but it must nevertheless be greater than a minimum value in order to avoid any risk of forming a succession of solid-gas pistons which would hinder proper heat exchange: for a dense fluidized bed 113 having a depth of 1.5 meters, the diameter of the closed vessel may be selected to be in the order of 1 meter.

In accordance with an essential aspect of the treatment method of the invention, the black powder to be treated 105 is inserted into the bottom of the heated fluidized bed 113, said bed having a predetermined effective depth h enabling the carbon on the particles of silica to be oxidized into carbon dioxide as the particles pass through the dense fluidized bed by being entrained by the fluidization air, with the then whitened powder 131 being recovered by filtering the gases that leave said dense fluidized bed.

There are therefore means 102 for injecting the powder to be treated and means 103 for storing it, which means are disposed close to the closed vessel 101 that contains the dense fluidized bed 113. The black powder to be treated as constituted by the silica fumes 105 is stored in a hopper 104 whose base is provided with a rotary metering lock (not shown) that feeds an injection channel 107 via a duct 106, the injection channel opening out into the side of the closed vessel 101 near the bottom thereof, i.e. near the bottom of the dense fluidized bed 113. As shown in the drawing, this can be done by means of a worm screw or auger 108 driven by an associated motor 109, the auger extending substantially horizontally and opening out into the closed vessel 101, preferably penetrating a short distance into said vessel (e.g. projecting 5 cm therein). Naturally, the Archimedes type worm screw 108 could be replaced by conveyor means for conveying a dense phase pneumatically, and suitable for overcoming the backpressure from the bed.

The black powder to be treated 105 is thus injected into the bottom of the dense fluidized bed 113, and this powder is temporarily "retained" by the layer of fluidized sand which ensures that it is kept in contact with the dense bed that is fluidized and heated to the desired temperature for an appropriate length of time to enable the carbon to be oxidized into carbon dioxide. By the time the powder reaches the surface 116 of the bed it no longer has any carbon and it escapes with the gases leaving the fluidized bed 113, so that it then suffices merely to organize an appropriate separation circuit for recovering the whitened powder 131.

It is interesting to observe that without having a dense fluidized bed of sand, the black powder to be treated would blow away at the upwards velocity of the fluidizing air. The fact that the powder is "retained" by the dense fluidized bed constitutes an original approach that goes against a prejudice of the person skilled in the art given that a fluidized layer of the powder per se would be impossible to treat.

There follows a description of the separator circuit that makes it easy to recover the whitened powder 131, said circuit comprising filter means 126 for filtering the gases coming from the dense fluidized bed 113, and recovery means 130 for recovering the whitened powder.

The outlet from the closed vessel 101 is constituted by a duct 122 leading to the inlet of a cyclone separator 123 whose outlet 124 is connected to a duct 125 leading to the inlet of the filter means 126. Thus, the inlet of the cyclone separator 123 is directly connected to the disengagement chamber 117 of the closed vessel 101, such that the gases leaving the dense fluidized bed 113 pass through the cyclone separator 123, thereby enabling any particles of sand to be returned to the dense bed 113 via an opening 141 provided between the bottom of the cyclone and the disengagement chamber 117, with the filtering for recovering the whitened powder then being performed downstream from the cyclone separator. It is preferable to select a cyclone separator having a cutoff diameter of about 30 μm, thereby ensuring that the whitened silica is not polluted with particles of sand.

The filter means 126 is preferably constituted by a bag filter 127 whose bottom portion terminates in a pressure-retaining rotary lock 128 having a receptacle 129 disposed therebeneath to constitute the recovery means, with the top portion of the filter means being connected via an associated duct 136 to an exhaust fan 137 that exhausts gases to a chimney 138. The rotary lock 128 includes an outlet orifice 135 through which the whitened powder 131 can flow, thus enabling it to be collected in the receptacle 129. The receptacle 129 is preferably a flexible sack or bag made of cloth which is closed at the bottom by a fastener 145 (single or multiple depending on whether the walls of the bag are single layer or multilayer), and having a top closure sheet 134 and handling straps 133. Such a bag is placed, in this case, on a support 132 prior to be being grasped by its straps 133. Bags of this type are commonly called "big bags" and are used in association with shipping containers: they provide a useful volume of about 1 m³ and they generally have a skin and a skirt constituting a double wall in association with four grasping straps, and two bottom fasteners that are merely opened in order to empty the bag.

The filter means 126 are preferably constituted by a bag filter 127 of conventional design having cloth filter bags (not shown) with a cutoff diameter that is preferably less than or equal to 1 μm. This type of filter is well known and includes its own mechanical unclogging system for shaking the bags, which system is also fitted with a recovery collector in the bottom portion of the filter. The rotary lock 128 enables the whitened powder 131 to be recovered without loosing the pressure that exists in the bag filter 127 (that is why it is referred to as a "pressure-retaining" lock). By using a bag filter of size comparable to the size specified above for the closed vessel 101, it is possible to use an NTP gas flow rate lying in the range 1000 m³/h to 2000 m³/h which, with the dimensions given above for the closed vessel 101 and for the depth of the dense fluidized bed contained in said vessel, makes it possible to treat at least 600 kg of powder per hour.

However, when using a bag filter having cloth bags, it is generally necessary to ensure that the temperature of the filtered gases does not exceed about 200° C. (even though some recent textile materials are capable of withstanding temperatures of as much as 240° C.). To this end, the duct 125 connecting the outlet of the cyclone separator 123 to the inlet of the bag filter 127 includes an open branch connection 139 for admitting cold dilution air into said duct. The temperature of the hot gases leaving the cyclone 123 can thus easily be reduced to about 150° C. by the time they reach the bag filter 127. The gases leaving the cyclone separator 123 are thus effectively diluted by the cool air to lower their temperature prior to being filtered for recovering the whitened powder 131. The branch connection 139 preferably includes a control member 140 such as a flap to control the quantity of dilution air that penetrates into the duct 125.

An installation of the type described requires an installed power of about 150 kW only. If a more powerful installation is desired, in particular for treating more than three tons per hour, then the installed power will exceed 500 kW and a larger diameter closed vessel will be used having injection means organized over a plurality of points distributed around the periphery of the closed vessel so that the particles are uniformly distributed over the section of the dense fluidized bed. When using a large diameter, it is generally also necessary to provide an immersed heater element so as to ensure that the dense fluidized bed is heated uniformly, as mentioned above.

In most cases, power of about 150 kW is sufficient for easily reaching a dense fluidized bed temperature lying in the range 550° C. to 750° C. by means of electrical heater jacket members disposed around the wall of the bed and radiating onto the closed vessel. The electrical heater jacket members could naturally be provided in the form of a stack of rings as a variant of the embodiment constituted by cylindrical shell portions as described above. The above temperature range is generally sufficient for completely oxidizing the carbon without changing the crystal state of the silica fumes. However, in some applications, it is nevertheless advantageous to be capable of treating silica fumes at a temperature of as much as 850° C., in particular since that makes it possible to offer cosmetic manufacturers with a product that differs slightly from the basic product with respect to its cristobalite content.

The above-described installation is easily controlled by using regulation based on the temperature difference measured by means of a temperature probe (not shown in the figures) between the temperature in a midlayer of the dense fluidized bed and the temperature at the bottom of the bed (e.g. a few cm from the support grid). While the measured temperature difference remains less than a threshold of 50° C., for example, then the fluidized state is achieved under good conditions. As soon as the difference exceeds this 20° C. threshold, a signal is transmitted to a controller which responds thereto by causing the fan that delivers fluidization air to increase its flow rate. An appropriate regulation algorithm will then provide for an alarm to be raised or for the installation to be stopped if the fluidized state is not achieved within a given length of time.

Such temperature regulation makes it possible to ensure that the dense fluidized bed remains permanently at a uniform temperature throughout its mass, thereby ensuring that the substance to be treated is subjected to a uniform and large thermal shock by being raised suddenly to a high temperature (within about 1 second), with such a thermal shock naturally being very favorable for oxidizing all of the particles of carbon.

The above-described installation having the dimensions as specified above requires a ground area of about 30 m² only, and a height of about 10 m. Its electrical power requirements are also moderate since an installation of this type merely requires connecting to three phase electricity at 380 volts and at a power of 200 kVA. Automatic control is advantageous insofar as the installation does not require personnel to run it. Maintenance personnel are merely warned by the remote control equipment of the installation in the event of faulty operation. On an industrial site, the installation may be connected to the rest of the factory via automated devices for feeding silica fumes into its hopper and for collecting its finished product.

Naturally, the method and the apparatus described above merely constitute one particular non-limiting example, and may be modified by using equivalent means or conditions. In particular, the cyclone separator may be omitted by providing a greatly flared ceiling above the bed with gases being recovered at a considerable height (about 10 meters). Nevertheless such an installation would naturally be taller.

The method and the apparatus of the invention are particularly suitable for use in the field of cosmetics. The powder recovered at the end of the treatment to which it is subjected is of a satisfactory white color while still retaining very fine grain size that is instrumental in obtaining the desired effect of smoothness in cosmetics, in particular foundation make-ups and face powders. In addition, the treatment method of the invention makes it possible to preserve the spherical shape of the particles of whitened silica and that is highly favorable in obtaining a high degree of smoothness.

The invention is not limited to the embodiments described above, but on the contrary it extends to any variant that reproduces the essential characteristics specified above by equivalent means.

I claim:

1. A method for treating blackened silica fumes for whitening purposes, where said blackened silica fumes comprise a plurality of silica particles coated with carbon, said method comprising the steps of:
   injecting said blackened silica fumes having a diameter less than one micrometer into a heated dense fluidized bed including a plurality of sand particles, said dense bed having a depth determines by a means grain size of said plurality of silica particles;
   oxidizing the carbon with fluidization air while the silica fumes pass through the dense fluidized bed; and
   recovering said plurality of silica particles having said diameter less than one micrometer which have passed through said dense fluidized bed.

2. A method according to claim 1, wherein the dense bed is a bed of sand whose effective depth is selected as a function of the mean diameter of the particles of silica to be treated.

3. A method according to claim 2, wherein the mean diameter of the particles of sand constituting the dense bed is about 400 μm.

4. A method according to claim 3, wherein the effective depth of the dense bed is about 1.5 meters when said bed is fluidized.

5. A method according to claim 1, wherein the dense bed is heated by electrical heating.

6. A method according to claim 5, wherein the dense bed is heated over its entire effective depth in such a manner that the fluidization air oxidizes the carbon present in the silica fumes, while the temperature of said dense bed remains below a sintering temperature of the silica fumes.

7. A method according to claim 5, wherein the temperature of the dense bed may be adjusted between 550° C. to about 850° C. so as to oxidize all of the carbon without changing the crystal state of the silica fumes.

8. A method according to claim 2, wherein the gases coming from the dense fluidized bed pass through a cyclone separator which returns any particles of sand to the dense bed and recovers the silica particles.

9. A method according to claim 8, wherein the cyclone separator recovers said silica particles by selecting a cutoff diameter of about 30 μm.

10. A method according to claim 8, wherein the gases leaving the cyclone separator are subjected to dilution with cold air to reduce their temperature prior to said gases being filtered for recovering the silica particles.

11. A method according to claim 10, wherein the temperature of the gases is reduced at least to 150° C. prior to filtering.

12. A method for treating blackened silica fumes for whitening purposes, where said blackened silica fumes comprise a plurality of silica particles coated with carbon, said method comprising the steps of:
   injecting said blackened silica fumes having a diameter less than one micrometer into a dense fluidized bed, said fluidized bed including a plurality of sand particles, wherein each of said plurality of sand particles having a diameter greater than 30 micrometers;
   oxidizing the carbon with fluidization air while the silica fumes pass through the dense fluidized bed having a depth determinable by a mean grain size of said plurality of silica particles;
   recovering said plurality of silica particles having said diameter less than one micrometer which have passed through said fluidized bed.

13. A method for treating blackened silica fumes for whitening purposes, where said blackened silica fumes comprise a plurality of silica particles coated with carbon, said method comprising the steps of:
   injecting said blackened silica fumes having a diameter less than one micrometer into a dense fluidized bed, said fluidized bed including a plurality of sand particles, wherein each of said plurality of sand particles having a means grain size of approximately 400 micrometers;
   oxidizing the carbon with fluidization air while the silica fumes pass through the dense fluidized bed having a depth of 1.5 meters, said depth being a function of said means grain size of said plurality of sand particles; and
   recovering said plurality of silica particles having such a diameter less than one micrometer which said dense fluidized bed through filtration.

* * * * *